United States Patent
Biedermann et al.

(10) Patent No.: US 9,289,245 B2
(45) Date of Patent: *Mar. 22, 2016

(54) LOCKING ASSEMBLY FOR A POLYAXIAL BONE ANCHORING DEVICE

(71) Applicant: Biedermann Technologies GmbH & Co. KG, Donaueschingen (DE)

(72) Inventors: Markku Biedermann, Miami, FL (US); José Santiago, Miami, FL (US)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/290,372

(22) Filed: May 29, 2014

(65) Prior Publication Data

US 2014/0350607 A1 Nov. 27, 2014

Related U.S. Application Data

(63) Continuation of application No. 13/663,171, filed on Oct. 29, 2012, now Pat. No. 8,771,320.

(60) Provisional application No. 61/552,554, filed on Oct. 28, 2011.

(51) Int. Cl.
*A61B 17/70* (2006.01)

(52) U.S. Cl.
CPC .......... *A61B 17/7032* (2013.01); *A61B 17/7035* (2013.01); *A61B 17/7037* (2013.01)

(58) Field of Classification Search
CPC ........... A61B 17/7001; A61B 17/7032; A61B 17/7034; A61B 17/7035; A61B 17/7037; A61B 17/7038; A61B 17/704; A61B 17/7041; A61B 17/7043; A61B 17/7044; A61B 17/7046; A61B 17/844; A61B 17/8685
USPC ................... 606/264–279, 300–308
See application file for complete search history.

(56) References Cited

U.S. PATENT DOCUMENTS 6,835,196 B2  12/2004  Biedermann et al.
7,204,838 B2   4/2007  Jackson (Continued)

OTHER PUBLICATIONS

Extended European Search Report for European Application No. 12153894.6, European Search Report dated Mar. 6, 2012 and mailed Mar. 17, 2012 (7 pgs.).

*Primary Examiner* — Pedro Philogene
(74) *Attorney, Agent, or Firm* — Lewis Roca Rothgerber Christie LLP

(57) ABSTRACT

A locking assembly for securing a rod in a polyaxial bone anchoring device includes a first locking element having a first end, a second end, an outer surface with an external advancement structure, an inner wall, an internal advancement structure on the inner wall, and an engagement portion for a tool, and a second locking element having a first end configured to be oriented towards the first end of the first locking element, an opposite second end, an outer surface with an external advancement structure configured to cooperate with the internal advancement structure of the first locking element, and a portion at the second end having a width greater than a greatest width of the external advancement structure of the second locking element, wherein the second locking element is configured to move axially relative to the bone anchoring device at a speed different than the first locking element.

6 Claims, 3 Drawing Sheets

(56) References Cited

U.S. PATENT DOCUMENTS

| | | |
|---|---|---|
| 7,625,394 B2 * | 12/2009 | Molz et al. ............... 606/270 |
| 7,972,364 B2 * | 7/2011 | Biedermann et al. ........ 606/267 |
| 8,221,472 B2 | 7/2012 | Peterson et al. |
| 8,663,298 B2 * | 3/2014 | Keyer et al. ............... 606/305 |
| 8,771,320 B2 * | 7/2014 | Biedermann et al. ........ 606/278 |
| 2003/0100896 A1 | 5/2003 | Biedermann et al. |
| 2006/0149235 A1 | 7/2006 | Jackson |
| 2007/0043358 A1 | 2/2007 | Molz, IV et al. |

* cited by examiner

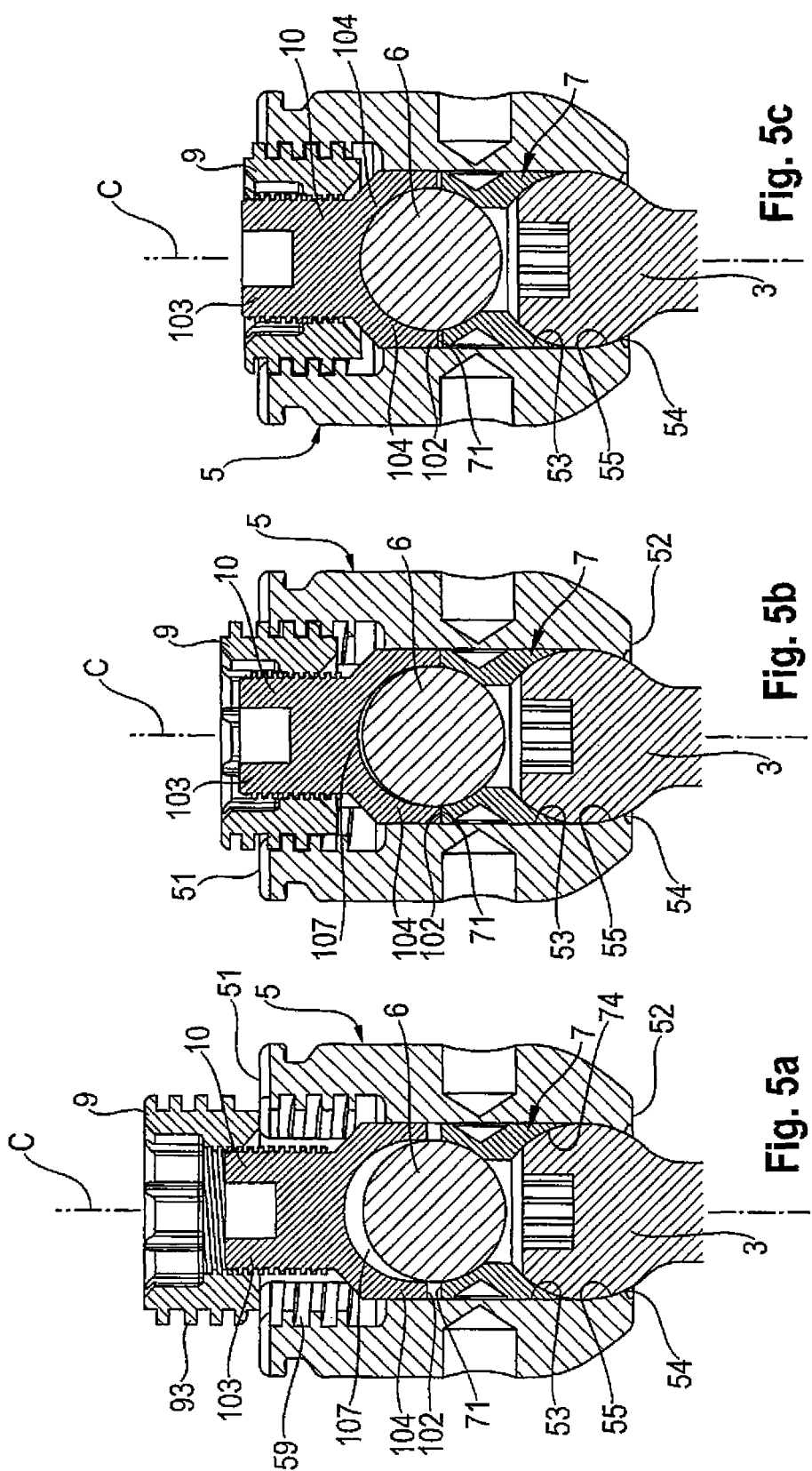

US 9,289,245 B2

LOCKING ASSEMBLY FOR A POLYAXIAL BONE ANCHORING DEVICE

CROSS-REFERENCE TO RELATED APPLICATION(S)

This application is a continuation of U.S. patent application Ser. No. 13/663,171, filed Oct. 29, 2012, which claims the benefit of U.S. Provisional Patent Application Ser. No. 61/552,554, filed Oct. 28, 2011, the contents of which are hereby incorporated by reference in their entirety.

BACKGROUND

1. Field of the Invention

The invention relates to a locking assembly for a polyaxial bone anchoring device for use in spinal or trauma surgery. The polyaxial bone anchoring device includes a bone anchoring element with a shank to be anchored in a bone and a head. The head is pivotably held in a receiving part and can be fixed at an angle relative to the receiving part by applying pressure onto the head via a pressure element. The receiving part has a recess with a substantially U-shaped cross-section for receiving a rod. Further, the locking assembly includes a first locking element that cooperates with the receiving part and is configured to fix the rod in the receiving part, and a second locking element configured to be arranged in the first locking element that is configured to fix the head via the pressure element. The first locking element has an engagement structure for a drive tool, and the second locking element is driven upon rotating the first locking element, so that the head and the rod can be fixed in a sequential manner using a tool with a single drive portion.

2. Description of Related Art

US 2003/0100896 A1 describes a bone anchoring device with a shank and a receiving part connected to it for connecting to a rod. The receiving part has a recess having a U-shaped cross-section for receiving the rod with two open legs and an internal thread on the open legs. A locking assembly is provided comprising a nut member with an external thread that cooperates with the internal thread of the legs and a set screw. The nut member has on one end slits for engagement with a screw tool. The shank has a spherically-shaped head that is pivotably held in the receiving part. A pressure element is provided that exerts pressure onto the head when the nut member is tightened. By tightening the set screw the rod is fixed in the receiving part. Hence, the rod and the head can be locked independently from each other.

U.S. Pat. No. 7,972,364 describes a locking assembly for securing a rod in a rod receiving part of a bone anchoring device that includes a first locking element and a second locking element. With the first locking element and the second locking element the head of the bone anchoring element and the rod can be locked independently using a tool with two drive portions.

SUMMARY

It is an object of embodiments of the invention to provide a locking assembly and a bone anchoring device with such a locking assembly that is simple to use and has advantages in certain applications.

The locking assembly according to embodiments of the invention is particularly applicable to polyaxial bone anchoring devices. It allows locking of a head of a bone anchoring element and a rod in a receiving part in a sequential manner using a single tool with a single drive portion. By this sequential locking mechanism, it is possible to first lock the head and thereafter finally lock the rod. In more detail, with embodiments of the locking assembly, first, a full locking of the head and the rod can be carried out, and thereafter, the fixation of the rod can be loosened to perform adjustments of the rod. Because only a single tool with a single drive portion is needed for performing these steps, the use of the locking assembly is more easily facilitated.

The locking principle of sequential, independent head and rod fixation according to embodiments of the invention is different from related art. The outer locking element serves for fixation of the rod and the inner locking element serves for fixation of the head. The inner locking element can transfer higher forces compared to the outer locking element. Therefore, the locking assembly can be designed to be more compact, which results in a more compact and more low profile design of the bone anchoring device.

Embodiments of the locking assembly cooperate with existing receiving parts that have an inner thread on a rod receiving portion of the receiving part. Therefore, the locking assembly according to embodiments of the invention can be used interchangeably with existing locking assemblies.

BRIEF DESCRIPTION OF THE DRAWINGS

Further features and advantages of the invention will become apparent from the description of embodiments by means of the accompanying drawings. In the drawings:

FIGS. 5a to 5c show steps of use of an embodiment of the locking assembly together with a polyaxial bone anchoring device.

DETAILED DESCRIPTION

Figure 1:
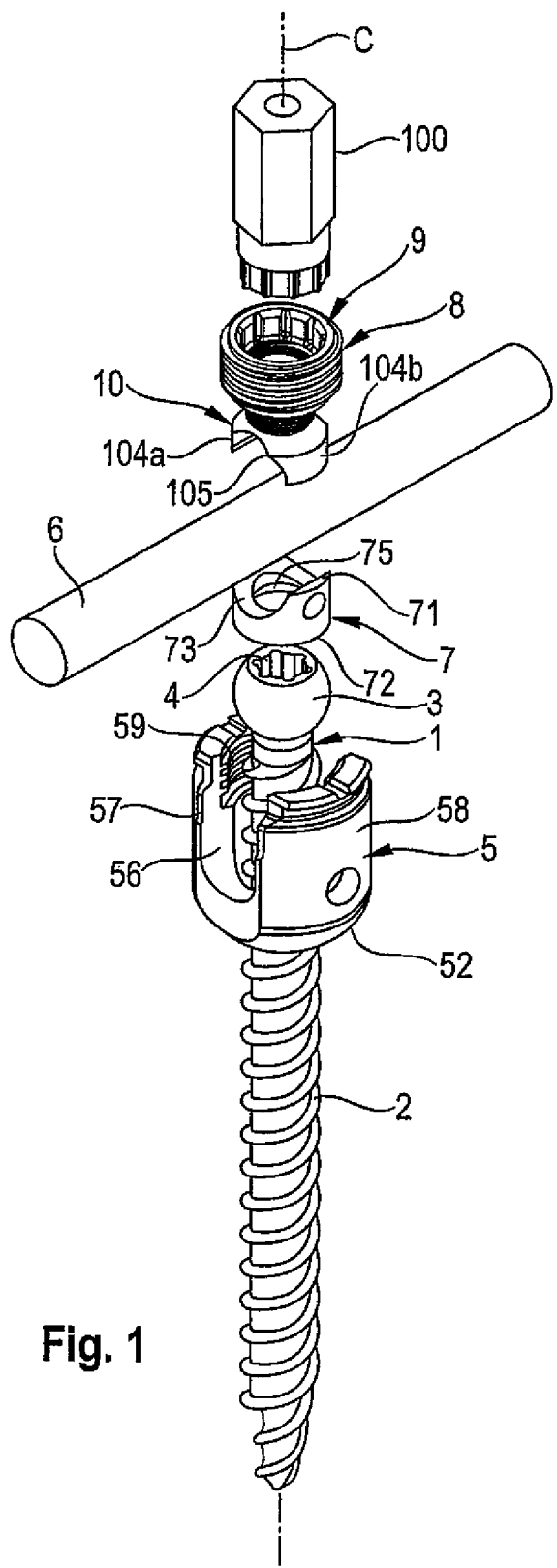
FIG. 1 shows a perspective exploded view of a bone anchoring device with a locking assembly according to an embodiment.

A polyaxial bone anchoring device according to an embodiment of the invention is shown in FIG. 1. The polyaxial bone anchoring device includes an anchoring element 1 having a shank 2 with a threaded portion and a head 3. The head 3 has a spherically-shaped outer surface portion and, on a side opposite to the shank 2, a recess 4 for engagement with a tool. A receiving part 5 is provided for coupling the bone anchoring element 1 to a rod 6. In the receiving part 5, a pressure element 7 can be arranged to exert pressure onto the head 3 of the bone anchoring element 1.

The bone anchoring device further includes a locking assembly 8 having a first locking element 9 and a second locking element 10 that can be coupled to the first locking element 9.

As shown in FIG. 1, to fix the rod 6 and lock the head 3, a tool 100 with a single drive portion may be provided that engages the first locking element 9.

Referring to FIG. 1 and FIGS. 5a to 5c, the receiving part 5 has a top end 51 and a bottom end 52, and includes portions having a substantially cylindrical construction, with a longitudinal axis C extending through the two ends 51, 52. Coaxial with the longitudinal axis C, a bore 53 is provided extending from the top end 51 to a predetermined distance from the bottom end 52. At the bottom end 52, an opening 54 is provided, a diameter of which is smaller than a diameter of the bore 53. The coaxial bore 53 tapers towards the opening 54. In the embodiment shown, the taper is in the form of a spherically-shaped section 55. However, the section 55 can have any other shape such as, for example, a conical shape, that facilitates the function of the head 3 being pivotably held in the receiving part 5, for example, similar to a ball and socket joint.

The receiving part 5 further has a U-shaped recess 56 extending from the top end 51 in the direction of the bottom end 52. By means of the U-shaped recess 56, two free legs 57, 58 are formed. The recess 56 is open towards the top end 51 and defines a channel for receiving the rod 6. Adjacent to the top end 51, an internal thread 59 is provided at inner surfaces of the legs 57, 58. In the embodiment shown, the internal thread 59 is a flat thread having substantially horizontal upper and lower thread flanks. However, any other thread form can be used for the internal thread 59, but, a thread form that reduces or eliminates splaying of the legs may be preferable, such as a flat thread or a negative angle thread. The internal thread 59 has a first thread pitch.

The pressure element 7 has a substantially cylindrical construction, with an outer diameter sized so as to allow the pressure element 7 to be introduced into the bore 53 of the receiving part 5 and to be moved therein in an axial direction. The pressure element 7 has a top end 71 and an opposite bottom end 72 and a longitudinal axis extending through the two ends, where the axis is coaxial with the longitudinal axis C of the receiving part 5 when the pressure element 7 is inserted therein. The pressure element 7 is arranged in the receiving part 5 such that its top end 71 is oriented towards the top end 51 of the receiving part and the bottom end 72 is oriented towards the bottom end 52 of the receiving part. At its top end 71, the pressure element has a cylindrically-shaped recess 73 that is configured to receive the rod 6. When the rod 6 rests in the recess 73, the top end 71 of the pressure element 7 does not extend past the surface of the rod 6 in a direction of the top end 51 of the receiving part 5. On its lower side, the pressure element 7 has a spherically-shaped recess configured to cooperate with the spherical outer surface portion of the head 3. Furthermore, a coaxial through-hole 75 is provided in the pressure element 7 that allows access to the recess 4 of the head 3, for example, by a tool, when the bone anchoring element 1 and the pressure element 7 are mounted to the receiving part 5.

Figure 2:
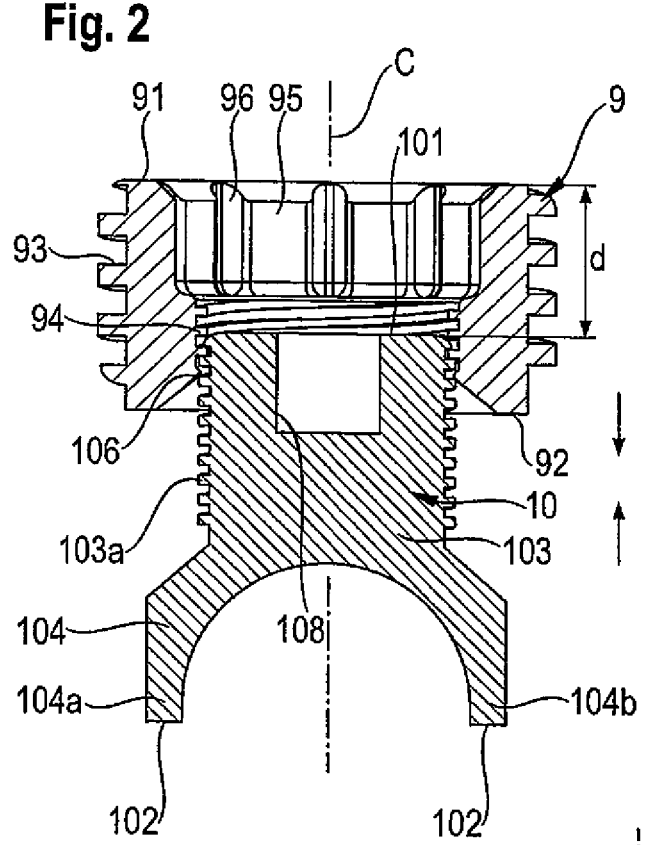
FIG. 2 shows a cross-sectional view of the locking assembly of FIG. 1, the cross-section taken in a plane perpendicular to an axis of an inserted rod.
Figure 3:
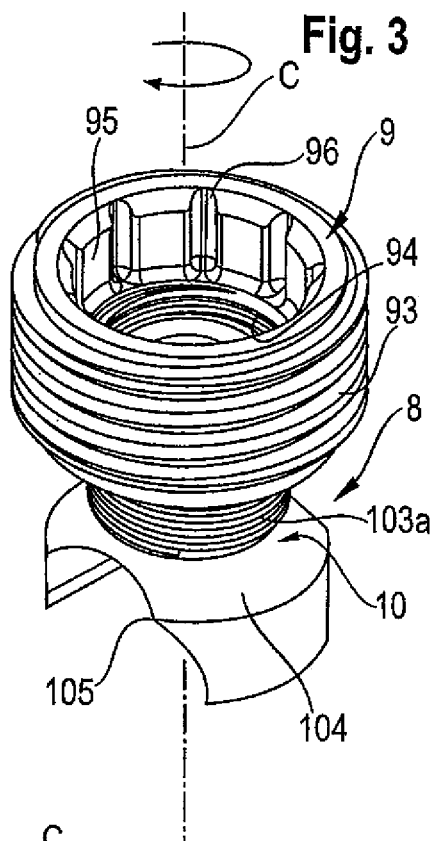
FIG. 3 shows an enlarged perspective view of the locking assembly of FIG. 1.

As can be seen in particular in FIGS. 2 and 3, the first locking element 9 of the locking assembly 8 is a screw, for example, a set screw, with a top end 91 and a bottom end 92. The first locking element 9 forms an outer locking element in the assembly 8. Between the top end 91 and the bottom end 92, an outer surface portion with an external thread 93 is provided that cooperates with the internal thread 59 of the receiving part 5. In the embodiment shown, the external thread 93 is a flat thread having a first thread pitch corresponding to the first thread pitch of the internal thread 59. A coaxial through-hole extends from the top end 91 to the bottom end 92, the through-hole has a portion with an internal thread 94 adjacent to the bottom end 92. The internal thread 94 has a second thread pitch that is smaller than the first thread pitch of the outer thread 93. The internal thread 94 is, in this embodiment, a flat thread. Thus, the thread 94 is capable of transferring high loads. The use of a flat thread as the internal thread 94 allows the first locking element to have a smaller size that contributes to a low profile bone anchoring device. Adjacent to the top end 91, a coaxial cylindrical recess 95 with an engagement structure 96 is provided that is engageable by the tool 100. The engagement structure 96 can be, for example, in the form of longitudinal grooves extending parallel to a central axis of the first locking element 9, like a torx-shape. The second thread pitch of the internal thread 94 can be, for example, three-quarters of the first thread pitch of the external thread 93. A relationship between the second thread pitch and the first thread pitch is selected such that a predefined advancement path for the first and second locking elements 9, 10, within the receiving part 5 is achieved.

The second locking element 10 forms an inner locking element of the assembly 8. The second locking element 10 has a top end 101 and a bottom end 102, a first portion 103 adjacent to the top end 101 and a second portion 104 between the first portion 103 and the bottom end 102. The first portion 103 is cylindrical with an outer surface portion having an external thread 103a that cooperates with the internal thread 94 of the first locking element 9. In the embodiment shown in FIGS. 1 to 3, the external thread 103a is a flat thread. The thread pitch of the external thread 103a corresponds to the second thread pitch. An axial length of the first portion 103 is such that when the second locking element 10 is fully engaged within the through-hole of the first locking element 9, the top end 101 of the second locking element 10 may be substantially flush with the top end 91 of the first locking element 9, as can be seen in particular in FIG. 5c. In other embodiments, the second locking element 10 may be farther above or below the top end 91 of the first locking element 9 when the first and second locking elements 9 and 10 are fully engaged.

The second portion 104 has a saddle-like shape with two outward and downward projecting saddle portions 104a, 104b that define a substantially U-shaped recess therebetween. The length of the saddle portions 104a, 104b are such that when the bottom end 102 is in contact with the top end 71 of the pressure element 7 and the rod 6 is placed between the saddle portions 104a, 104b and the pressure element 7, there is a gap 107 between a top of the saddle-shaped region and the rod 6, as shown in FIGS. 5a and 5b.

Referring to FIG. 3, on either side of each saddle portion 104a, 104b, two outwardly projecting edges 105 or projections are provided. More specifically, four edges 105 that project in a direction of the rod axis when the rod is inserted are provided. The edges 105 are located at a distance from the bottom end 102 and project outward to such an extent that when the second locking element 10 is mounted to the first locking element 9 and the locking assembly 8 is inserted into the receiving part 5, the edges 105 prevent rotation of the second locking element 10 with respect to the receiving part 5. Rotation of the second locking element 10 may be prevented because the edges 105 cause portions of outermost parts of the saddle portion 104 to form, for example, edges of a rectangle, which may abut against, for example, the internal thread 59, sides of the recess 56, or other portions of the bore 53 of the receiving part 5 when the second locking element 10 is in the receiving part 5. An outer diameter of lower portions of the saddle portions 104a, 104b adjacent the bottom end 102 is smaller than an inner diameter of the coaxial bore 53, so that the saddle portions 104a, 104b can extend into the coaxial bore 53, as can be seen in FIGS. 5a to 5c. Further, a small engagement portion 108 can be provided in the second locking element 10.

The locking assembly 8 may be preassembled in such a manner that the second locking element 10 is arranged with its first portion 103 within the first locking element 9, while the second portion 104, as well as a section of the first portion 103, projects outward from the bottom end 92 of the first locking element 9, as shown in FIGS. 2 and 3. The second locking element 10 may be fixed in a preliminary manner to the first locking element at a predetermined breaking point 106, which may be for example, a welding point that is provided near the bottom end 92 at a contact area between the external thread 103a of the second locking element 10 and the internal thread 94 of the first locking element 9. The welding point 106 has a fixation strength such that it can be broken by rotating the first locking element 9 with respect to the second locking element 10 using, for example, a handheld tool 100. By the preliminary fixation of the second locking element 10 to the first locking element 9, a predetermined height relationship or relative position between the second locking element 10 and the first locking element 9 can be provided and maintained before inserting the locking assembly 8 into the receiving part 5.

Figure 4:
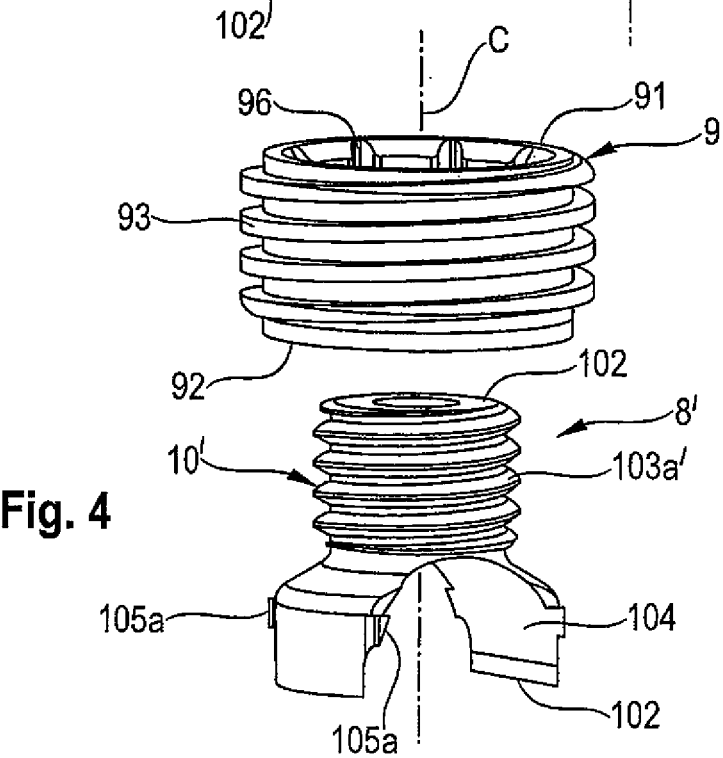
FIG. 4 shows a perspective exploded view of a modified locking assembly.

FIG. 4 shows a modified embodiment of the locking assembly. The locking assembly 8' differs from the locking assembly 8 described above in that the saddle portion 104 has at a distance from the bottom end 102 four tabs 105a' that prevent rotation when inserting the locking assembly 8' into the receiving part 5. The tabs 105a' have triangular cross sections. In addition, instead of a flat thread, a metric thread 103a' is used as the external thread for second locking element 10'. Other parts are the same or similar to the first embodiment.

The parts of the bone anchoring device are made of a biocompatible material, for example, of a biocompatible metal or metal alloy, such as titanium, stainless steel, of nickel titanium alloys, such as Nitinol, or of a biocompatible plastic material, such as PEEK (polyetheretherketone). The parts can be made of the same or of different materials.

A function or operation of the locking assembly 8 may be as follows. The locking assembly 8 is preassembled as shown in FIG. 2, wherein the top end 101 of the second locking element 10 is located at a distance d from the top end 91 of the first locking element 9 and is fixed with the welding point 106 in a preliminary manner. In use, when the locking assembly 8 is inserted into the receiving part 5 and the saddle 104 engages the rod 6, the second locking element 10 is prevented from rotation, and a clockwise rotation of the first locking element 9 allows the first locking element 9 to travel downward relative to the receiving part 5. Meanwhile, the second locking element 10 travels upward relative to the first locking element 9.

In use, the bone anchoring device is operated as follows. First, at least two bone anchoring devices including the bone anchoring element 1, the receiving part 5, and the pressure element 7, which may be preassembled are screwed into a bone or a vertebra. Thereafter, the rod 6 is inserted into the U-shaped recess 56 of the receiving part 5. Then, the locking assembly 8 that is preassembled as described above can be inserted between the legs 57, 58, until the external thread 93 of the first locking element 9 engages the internal thread 59 provided on the legs 57, 58. Torque applied to the first locking element 9 with the tool 100 will break the welding point 106 between the first locking element 9 and the second locking element 10, allowing the second locking element 10 to travel vertically relative to the first locking element 9. An initial position is shown in FIG. 5a. The first locking element 9 has not moved a full turn. In this position, the bottom end 102 of the second locking element 10 is not yet in contact with the top end 71 of the pressure element 7. Furthermore, there is a gap 107 between an upper surface of the rod 6 and an upper region of the saddle portion 104.

Then, as shown in FIG. 5b, after several turns of the first locking element 9, the first locking element 9 has travelled downwards. The first locking element 9 is still not in contact with the rod 6. Meanwhile, the second locking element 10 has travelled downwards a smaller distance than the first locking element 9 (e.g., due to the difference between the first and second pitches) and is now in contact with its saddle portions 104, 104b pressing onto the top end 71 of the pressure element 7. By means of this, the pressure element 7 exerts pressure onto the head 3 that clamps the head 3 by friction. Therefore, the bone anchoring element 1 can be maintained at a particular angular position with respect to the receiving part 5.

As can be seen in FIG. 5c, by further rotating the first locking element 9, the additional torque applied to the first locking element 9 causes the first locking element 9 to press onto the rod 6 and locks the full assembly of the bone anchoring device, that is, the head 3 and the rod 6 relative to the receiving part 5.

The travel paths of the locking elements 9, 10 can be determined as follows:

First locking element absolute travel path=number of turns*first pitch

Second locking element absolute travel path=number of turns*(first pitch−second pitch)

If the first pitch is 1 mm and the second pitch is 0.75 mm, and the number of turns is 1, then in one tightening turn, the first locking element will move 1 mm downwards and the second locking element will move 0.25 mm downwards.

After full locking of the head 3 and the rod 6, as shown in FIG. 5c, the fixation of the rod 6 may be loosened by turning back the first locking element 9, to allow adjustments of the rod 6 while the head 3 remains locked. Hence, in a sequential procedure, first, the whole assembly is locked, and then, the position of the rod 6 can be adjusted using only one tool with a single drive portion.

Various modifications of the embodiments described are also conceivable. For the polyaxial bone anchoring device, any known polyaxial bone anchoring device can be used that includes a bone anchoring element pivotably received and a rod received in a receiving part. For a bone anchoring element, any known bone anchors, such as screws, nails, hooks, among others, can be used. In addition, for example, the pressure element and/or the second portion of the second locking element may be shaped differently. For example, the pressure element can be designed with a flat upper surface that contacts the rod. In such a case, the saddle portions of the second locking element may be longer to contact the pressure element without contacting the rod at its highest surface point. Alternatively, for example, the recess where the rod is received in the pressure element can be deeper, and can have such a depth that the top end 71 of the pressure element extends above the top surface of the rod. In such a case, the saddle portions of the second locking element can be shorter. Meanwhile, the second portion of the second locking element may be rotatably coupled to the first portion of the second locking element. The internal thread of the first locking element and the external thread of the first locking element may run in opposite directions. Various other modifications may also be implemented.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A method of coupling a rod to a bone or vertebra via a polyaxial bone anchoring device, the bone anchoring device comprising a bone anchoring element having a shank and a head, a receiving part configured to be coupled to the bone anchoring element and to pivotably receive the head, the receiving part having a recess with a substantially U-shaped cross-section for receiving the rod, the recess defining two legs, the legs having an internal advancement structure, a pressure element configured to contact the head to exert pressure on the head to lock an angular position of the head relative to the receiving part, and a locking assembly comprising a first locking element having a longitudinal axis, an outer surface with an external advancement structure configured to cooperate with the internal advancement structure of the legs, an inner wall defining a coaxial bore extending through the first locking element along the longitudinal axis, an internal advancement structure on a portion of the inner wall, and an engagement portion for a tool for advancing the first locking element relative to the receiving part, and a second locking element configured to be arranged at least partially in the first locking element, the second locking element having an outer surface with an external advancement structure configured to cooperate with the internal advancement structure of the first locking element, the method comprising:

inserting the shank of the bone anchoring element into a bone or vertebra;
   adjusting the angular position of the receiving part relative to the bone anchoring element;
   inserting a rod into the recess of the receiving part, wherein the pressure element is positioned between the head and the rod;
   inserting the locking assembly into the recess;
   advancing the locking assembly in the receiving part towards the head, such that the first locking element is advanced axially in the receiving part at a first speed, and the second locking element moves axially relative to the receiving part at a speed different than the first speed, until the second locking element locks the head relative to the receiving part and the first locking element locks the rod relative to the receiving part.

2. The method of claim 1, wherein the respective advancement structures of the first locking element and the second locking element comprise threads, and wherein advancing the locking assembly in the receiving part comprises rotating the first locking element in a first direction relative to the receiving part while the second locking element is prevented from rotating relative to the receiving part.

3. The method of claim 2, further comprising:
   rotating the first locking element in a direction opposite the first direction until the rod is unlocked while the head remains locked;
   adjusting a position of the rod relative to the receiving part; and
   rotating the first locking element in the first direction until the rod is locked.

4. The method of claim 2, wherein the first and second locking elements are temporarily fixed relative to one mother via a connection, and wherein when the first locking element is rotated relative to the receiving part while the second locking element is prevented from rotating relative to the receiving part, the connection between the first and second locking elements is separated.

5. The method of claim 1, wherein the pressure element is inserted in the receiving part prior to inserting the shank into the bone or vertebra.

6. The method of claim 1, wherein the pressure element is inserted in the receiving part after inserting the shank into the bone or vertebra.

* * * * *